US012594404B2

(12) United States Patent
Ushida et al.

(10) Patent No.: US 12,594,404 B2
(45) Date of Patent: Apr. 7, 2026

(54) GUIDE WIRE

(71) Applicant: ASAHI INTECC CO., LTD., Seto (JP)

(72) Inventors: Keisuke Ushida, Seto (JP); Masahiro Kashiwai, Seto (JP)

(73) Assignee: ASAHI INTECC CO., LTD., Seto (JP)

( * ) Notice: Subject to any disclaimer, the term of this patent is extended or adjusted under 35 U.S.C. 154(b) by 598 days.

(21) Appl. No.: 17/982,672

(22) Filed: Nov. 8, 2022

(65) Prior Publication Data

US 2023/0061060 A1 Mar. 2, 2023

Related U.S. Application Data

(63) Continuation of application No. PCT/JP2020/018652, filed on May 8, 2020.

(51) Int. Cl.
A61M 25/09 (2006.01)

(52) U.S. Cl.
CPC ... A61M 25/09 (2013.01); *A61M 2025/09083* (2013.01); *A61M 2025/09108* (2013.01); *A61M 2025/09191* (2013.01)

(58) Field of Classification Search
CPC ........ A61M 25/09; A61M 2025/09083; A61M 2025/09108; A61M 2025/09191; A61M 25/09016; A61M 2025/09133
See application file for complete search history.

(56) References Cited

U.S. PATENT DOCUMENTS

| 2002/0049392 | A1 | 4/2002 | DeMello |
| 2010/0318065 | A1 | 12/2010 | Miyata et al. |
| 2012/0253321 | A1 | 10/2012 | Tsunezumi |

FOREIGN PATENT DOCUMENTS

| CN | 101920056 A | 12/2010 |
| CN | 102727984 A | 10/2012 |
| JP | H09-182800 A | 7/1997 |

OTHER PUBLICATIONS

Jun. 16, 2020 International Search Report issued in International Patent Application No. PCT/JP2020/018652.

*Primary Examiner* — Tse W Chen
(74) *Attorney, Agent, or Firm* — Oliff PLC

(57) ABSTRACT

A guide wire including a core shaft including a distal end portion having a pseudoelastic property, a tip joined to a distal end of the distal end portion of the core shaft, and an auxiliary wire that is arranged parallel to the distal end portion of the core shaft. The auxiliary wire has a distal end joined to the tip and a rear end joined to the core shaft. The auxiliary wire has a high flexibility, a high breaking strength, and a short breaking elongation compared to the distal end portion of the core shaft.

4 Claims, 2 Drawing Sheets

GUIDE WIRE

CROSS REFERENCE TO RELATED APPLICATION

This application is a continuation application of International Application No. PCT/JP2020/018652, filed May 8, 2020. The content of this application is incorporated herein by reference in its entirety.

TECHNICAL FIELD

This application relates to a guide wire to be inserted into a blood vessel, or the like.

BACKGROUND

Methods using a catheter are widely implemented as a method for treating or examining a constricted part or occluded part (hereinafter referred to as "lesion") in a blood vessel, or the like. Typically, guide wires are used to guide the catheter to the lesion in the blood vessel, or the like. The guide wire needs to be able to enter the blood vessel along the curvature of the blood vessel, and a distal end portion of the guide wire needs to have flexibility. When the lesion hardens due to calcification, or the like, and the distal end portion of the guide wire gets stuck in the lesion, the load is applied to the distal end portion of the guide wire so as to remove the distal end portion of the guide wire from the lesion, and therefore it is necessary to prevent the breakage of the distal end portion of the guide wire.

The guide wire includes a core shaft and a tip joined to a distal end of the core shaft. In some guide wires, the core shaft has a superelastic property, and further a safety wire is provided (see, for example, Patent Literature 1). The safety wire made of a non-superelastic material is arranged parallel to the distal end portion of the core shaft made of a superelastic material such as NiTi, the distal end of the safety wire is joined to the tip, and the rear end of the safety wire is joined to the core shaft. Even when the core shaft is broken, the broken portion may be prevented from remaining in the body as the broken part is coupled to a main body of the core shaft via the safety wire.

CITATION LIST

Patent Literature

U.S. Patent Application Publication No. 2002/0049392

SUMMARY

Technical Problem

In the conventional configuration including the safety wire, the flexibility of the distal end portion of the guide wire and the safety wire has not been fully considered. The conventional configuration described above includes the safety wire to safely extract the distal end portion of the guide wire after the distal end portion of the core shaft is broken. In this conventional configuration, the core shaft is broken before the break of the safety wire, and then the safety wire bears the tensile load when the guide wire is removed from the lesion, and in order not to break the safety wire due to the tensile load, the safety wire needs to have a large outer diameter. As the flexibility of the safety wire decreases in accordance with an increase in the outer diameter, there is a possibility of a reduction in the flexibility of the distal end portion of the guide wire due to the presence of the safety wire.

The disclosed embodiments provide a solution to the issues described above.

Solution to Problem

The disclosed embodiments may be implemented according to the aspects below. The disclosure is not intended to be limited to these specific embodiments.

(1) The guide wire according to disclosed embodiments is a guide wire including a core shaft including a distal end portion having a pseudoelastic property, a tip joined to a distal end of the distal end portion of the core shaft, and an auxiliary wire that is arranged parallel to the distal end portion of the core shaft, has a distal end joined to the tip, and has a rear end joined to the core shaft, and the auxiliary wire has a high flexibility, a high breaking strength, and a short breaking elongation as compared with the distal end portion of the core shaft.

In the guide wire, the distal end portion of the core shaft has a pseudoelastic property. Therefore, as compared with the configuration in which, for example, the distal end portion is made of a material not having a pseudoelastic property, such as stainless steel, it is possible to prevent the breakage of the core shaft when the distal end portion is elongated due to the tensile stress applied. Furthermore, the auxiliary wire is arranged parallel to the distal end portion of the core shaft, and the auxiliary wire is more flexible than the distal end portion of the core shaft. Thus, with the guide wire, the auxiliary wire may prevent the breakage of the core shaft, while it is possible to prevent a decrease in the flexibility of the distal end portion of the core shaft due to the presence of the auxiliary wire. As compared with the configuration in which the breaking strength of the auxiliary wire is equal to or less than the breaking strength of the distal end portion of the core shaft, the breakage of the core shaft may be prevented more effectively. As compared with the configuration in which the breaking elongation of the auxiliary wire is equal to or more than the breaking elongation of the distal end portion of the core shaft, the application of the tensile stress only to the core shaft is prevented so that the breakage of the distal end portion of the core shaft may be prevented more effectively.

(2) In the above-described guide wire, the configuration may be such that the breaking elongation of the auxiliary wire is shorter than an elongation at a yield point of the distal end portion of the core shaft. In the guide wire, the breaking elongation of the auxiliary wire is shorter than the elongation at the yield point of the distal end portion of the core shaft. This prevents the distal end portion of the core shaft from reaching the yield point and maintains the elastic deformation state and, as a result, plastic deformation of the core shaft may be prevented.

(3) In the above-described guide wire, the configuration may be such that the auxiliary wire has the configuration in which a plurality of strands is twisted together. In the guide wire, the auxiliary wire has the configuration in which a plurality of strands is twisted together. Thus, the flexibility of the auxiliary wire is maintained, while the breaking strength of the auxiliary wire may be improved. Thus, the flexibility of the distal end portion of the above guide wire may be ensured. With respect to the tensile load, the elongation occurs not only in the strands themselves, but also due to the reduced distance between the twisted strands, and therefore there may be an increase in the amount of elongation before breakage as compared with a solid wire made of the same material as the auxiliary wire. By adjusting the twisting density of strands, the amount of elongation before the auxiliary wire is broken may be adjusted.

The disclosed embodiments may be realized in various forms, for example, in the form of a guide wire, a manufacturing method thereof, etc.

DETAILED DESCRIPTION

A. Embodiment

A-1. Basic Configuration of Guide Wire 100

Figure 1:
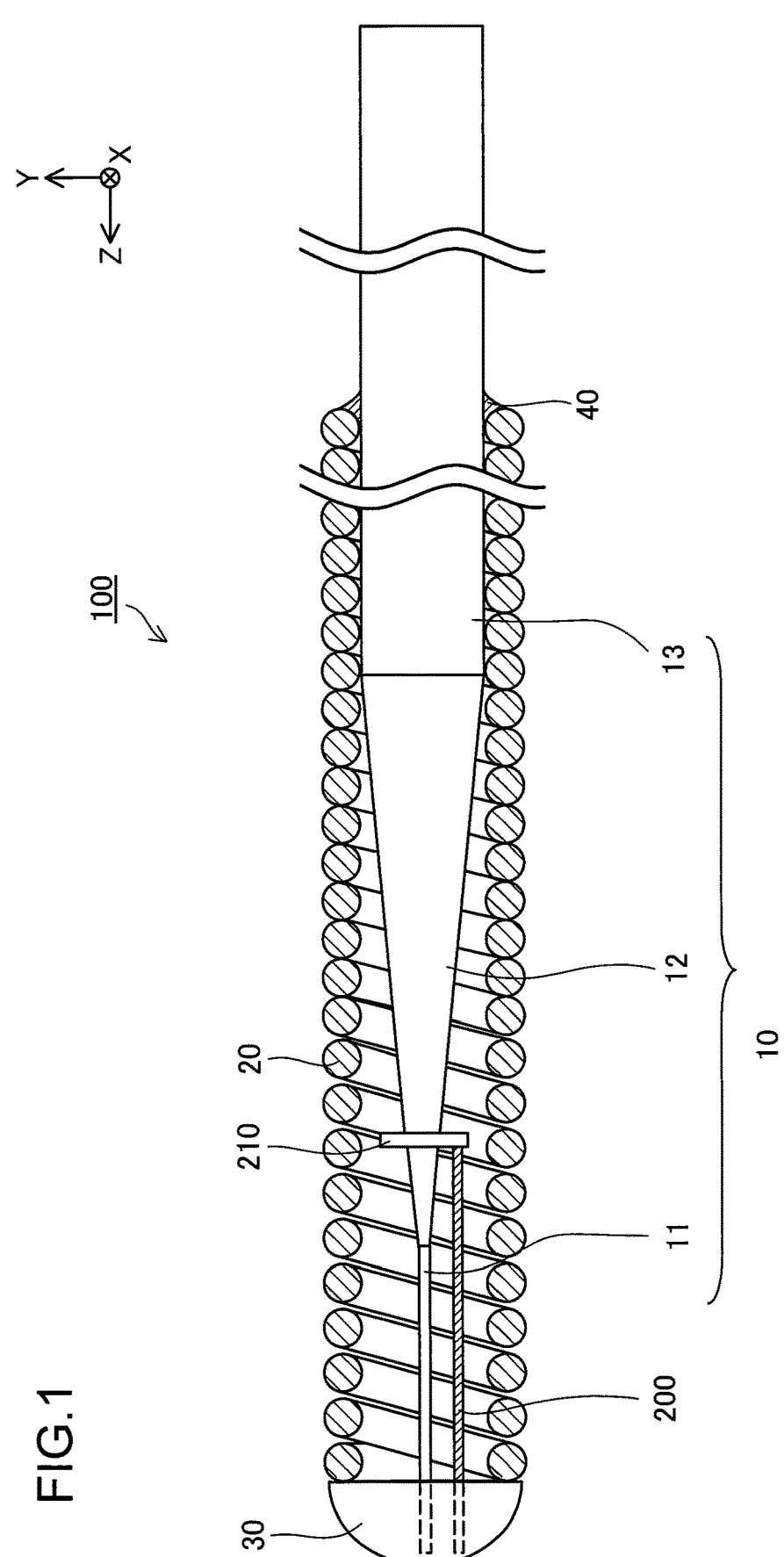
FIG. 1 is an explanatory diagram schematically illustrating a configuration of a guide wire 100 according to an embodiment.

FIG. 1 is an explanatory diagram schematically illustrating a configuration of a guide wire 100 according to the present embodiment. FIG. 1 illustrates a configuration of a longitudinal cross-section (YZ cross-section) of the guide wire 100. FIG. 1 illustrates a side configuration for portions of the guide wire 100 other than a coil body 20 described below. A part of the guide wire 100 is not illustrated in FIG. 1. In FIG. 1, a Z-axis positive direction side is a distal end side (far side) inserted into the body, and a Z-axis negative direction side is a proximal end side (near side) manipulated by a technician such as a physician. FIG. 1 illustrates a state where the guide wire 100 has a straight shape substantially parallel to a Z-axis direction as a whole, but the guide wire 100 is flexible enough to be curved.

In this description, for convenience of explanation, the guide wire 100 is assumed to be in the state illustrated in FIG. 1, and the Z-axis direction is referred to as the "axial direction of the guide wire 100" or simply as the "axial direction".

The guide wire 100 is an elongated medical device inserted into a blood vessel, or the like, to guide a catheter into a lesion (constricted part or occluded part) in the blood vessel, or the like. The total length of the guide wire 100 is, for example, approximately 1500 mm or more and 2000 mm or less, and the outer diameter of the guide wire 100 is, for example, approximately 0.5 mm or more and 1.2 mm or less.

The guide wire 100 includes a core shaft 10, the coil body 20, a tip 30, and an auxiliary wire 200.

The core shaft 10 is an elongated member whose distal end side has a small diameter and proximal end side has a large diameter. More specifically, the core shaft 10 includes a rod-shaped small diameter portion 11, a rod-shaped large diameter portion 13 that is located on the proximal end side with respect to the small diameter portion 11 and has a diameter larger than that of the small diameter portion 11, and a tapered portion 12 that is located between the small diameter portion 11 and the large diameter portion 13 and has a diameter gradually increasing from a boundary position with the small diameter portion 11 to a boundary position with the large diameter portion 13. According to the present embodiment, the outer diameter of the small diameter portion 11 is smaller than the outer diameter of the distal end of the tapered portion 12. As the small diameter portion 11 of the core shaft 10 is thin as described above, high flexibility of the small diameter portion 11 is ensured. The shape of the cross-section (XY cross-section) at each position of the core shaft 10 may be any shape, such as a circular shape or a flat-plate shape. The outer diameter of the large diameter portion 13 is, for example, approximately 0.2 mm or more and 0.6 mm or less. The outer diameter of the small diameter portion 11 is, for example, approximately 150 μm or less.

The core shaft 10 has a pseudoelastic property. The pseudoelastic property here refers to the apparent elastic property that occurs in a mechanism such as twinning deformation other than the elasticity resulting from changes in interatomic spacing and include shape memory effect and superelasticity (transformation pseudoelasticity or twinning pseudoelasticity). The examples of the material for forming the core shaft 10 include Ni—Ti alloys having a pseudoelastic property, Ni—Ti based alloys, etc. More specifically, they are superelastic metals (Ni—Ti alloys), work-hardened Ni—Ti based alloys, wide strain range elastic Ni—Ti based alloys, linear elastic Ni—Ti based alloys, etc. Ni—Ti alloys having a pseudoelastic property and Ni—Ti based alloys are Ni—Ti alloys in which the Ni content is 48 at % or more and 52.0 at % or less and the remainder is Ti, Ni—Ti based alloys in which the Ni content is 48.0 at % or more and 52.0 at % or less, the content of one or more of Cr, Fe, Co, Mo, V, and Al is 0.05 at % or more and 3.0 at % or less, and the remainder is Ti, Ni—Ti based alloys in which the Ni content is 36.0 at % or more and 48.0 at % or less, the Cu content is 5.0 at % or more and 12.0 at % or less, and the remainder is Ti, etc. The entire core shaft 10 may be made of the same material, or each portion may be made of a different material from each other. For example, the distal end portion of the core shaft 10 may be made of a material having a pseudoelastic property, and the other portions may be made of materials having no pseudoelastic property.

The coil body 20 is a coiled member formed in a hollow cylindrical shape by spirally winding a strand. The coil body 20 is wound around a portion of the core shaft 10 on the distal end side. The portion of the guide wire 100 around which the coil body 20 is wound is primarily a portion inserted into the body. According to the present embodiment, the coil body 20 has the configuration of one strand tightly wound.

As the material for forming the coil body 20, known materials are used, such as metallic materials, more specifically, stainless steel (SUS302, SUS304, SUS316, etc.), superelastic alloys such as Ni—Ti alloys, piano wires, nickel-chromium based alloys, cobalt alloys, tungsten, and the like, are used.

The tip 30 is a member that joins the distal end of the core shaft 10 and the distal end of the coil body 20. Specifically, the distal end of the core shaft 10 and the distal end of the coil body 20 are firmly attached so as to be embedded inside the tip 30. The outer peripheral surface of the tip 30 on the distal end side is a smooth surface (e.g., substantially a hemispherical surface). A coil joint part 40 is a member that joins the core shaft 10 and the proximal end of the coil body 20 at a predetermined position between the proximal end and the distal end of the core shaft 10 along the axial direction.

The auxiliary wire 200 is arranged parallel to the distal end portion of the core shaft 10. Specifically, the auxiliary wire 200 is a linear member that is located on the outer periphery side of the distal end portion of the core shaft 10 and extends along the axial direction. According to the present embodiment, when viewed from the axial direction, the auxiliary wire 200 is located between the distal end portion of the core shaft 10 and the coil body 20. The distal end of the auxiliary wire 200 is joined to the tip 30, and the rear end of the auxiliary wire 200 is joined to the tapered portion 12 of the core shaft 10 via a wire joint part 210. The wire joint part 210 is formed over the entire circumference of the core shaft 10 (the tapered portion 12). The portion from the distal end of the core shaft 10 to the position of the wire joint part 210 is an example of the distal end portion of the core shaft in claims. The relationship between the distal end portion of the core shaft 10 and the auxiliary wire 200 will be described below.

The material for forming the auxiliary wire 200 is, for example, metallic materials, more specifically, stainless steel (SUS302, SUS304, SUS316, etc.), piano wires, nickel-chromium based alloys, cobalt alloys, tungsten, and the like, are used. The auxiliary wire 200 may be made of the same material as that of the distal end portion of the core shaft 10.

As the materials for forming the tip 30, the coil joint part 40, and the wire joint part 210, known materials are used and, for example, soldering materials (aluminum alloy solder, silver solder, gold solder, etc.), metal solders (Ag—Sn alloys, Au—Sn alloys, etc.), adhesives (epoxy based adhesives, etc.), and the like, are used.

Part or all of the guide wire 100 may be coated with a known coating agent.

A-2. Relationship Between Distal End Portion of Core Shaft 10 and Auxiliary Wire 200

Next, the relationship between the distal end portion of the core shaft 10 and the auxiliary wire 200 in the guide wire 100 according to the present embodiment will be described. First, the auxiliary wire 200 satisfies a first requirement below.

<First Requirement>

The auxiliary wire 200 is more flexible than the distal end portion of the core shaft 10.

The auxiliary wire 200 preferably satisfies a second requirement below.

<Second Requirement>

The breaking strength of the auxiliary wire 200 is higher than the breaking strength of the distal end portion of the core shaft 10.

The auxiliary wire 200 preferably satisfies a third requirement below.

<Third Requirement>

The breaking elongation of the auxiliary wire 200 is shorter than the breaking elongation of the distal end portion of the core shaft 10.

The auxiliary wire 200 preferably satisfies a fourth requirement below.

<Fourth Requirement>

The breaking elongation of the auxiliary wire 200 is shorter than the elongation at a yield point P1 of the distal end portion of the core shaft 10.

The auxiliary wire 200 preferably satisfies a fifth requirement below.

<Fifth Requirement>

The auxiliary wire 200 has the configuration in which a plurality of strands is twisted together.

Here, an example of the relationship between the distal end portion of the core shaft 10 and the auxiliary wire 200 will be described. The distal end portion of the core shaft 10 is made of, for example, a material (such as Ni—Ti alloy) having a superelastic property. The auxiliary wire 200 is a wire having the configuration in which a plurality of strands, which has the outer diameter smaller than that of the distal end portion of the core shaft 10, is twisted together. The strand is made of, for example, stainless steel. The outer diameter of the auxiliary wire 200 itself is also smaller than the outer diameter of the distal end portion (the small diameter portion 11) of the core shaft 10.

Figure 2:
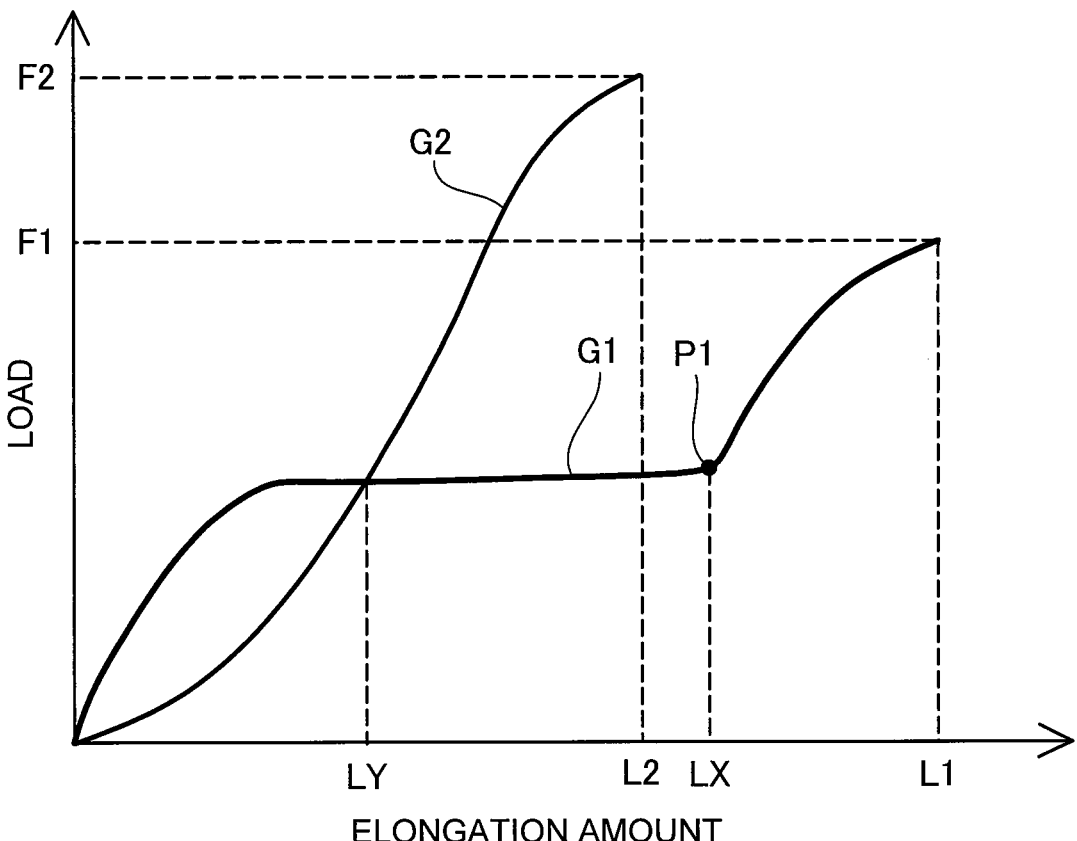
FIG. 2 is an explanatory diagram Illustrating the relationship between a distal end portion of a core shaft 10 and an auxiliary wire 200.

FIG. 2 is an explanatory diagram illustrating the relationship between the distal end portion of the core shaft 10 and the auxiliary wire 200. FIG. 2 illustrates graphs of the relationships between the load (tensile load) and the amount of elongation in the distal end portion of the core shaft 10 and the auxiliary wire 200, respectively. A first graph G1 is a graph of the relationship between the load and the amount of elongation in the distal end portion of the core shaft 10. A second graph G2 is a graph of the relationship between the load and the amount of elongation in the auxiliary wire 200.

As described above, the distal end portion of the core shaft 10 is made of a material having a superelastic property. Therefore, in the first graph G1, an elastic region (a region where the amount of elongation is equal to or less than LX) and a plastic region (a region where the amount of elongation is more than LX) are present in the distal end portion of the core shaft 10. P1 in the first graph G1 is a yield point (also referred to as the elastic limit point) that is the boundary between the elastic region and the plastic region. In the elastic region, there are a linear elastic region and a plateau region. The linear elastic region is a region where the tensile load applied to the distal end portion of the core shaft 10 is substantially proportional to the amount of elongation of the distal end portion of the core shaft 10. The plateau region is a region where the amount of elongation of the distal end portion of the core shaft 10 increases while the tensile load applied to the distal end portion of the core shaft 10 is substantially constant.

In the auxiliary wire 200, as illustrated in the second graph G2, the amount of elongation of the auxiliary wire 200 increases as the tensile load applied to the auxiliary wire 200 increases. As described above, the auxiliary wire 200 has the configuration in which a plurality of strands made of stainless steel is twisted together. Therefore, the auxiliary wire 200 is more flexible than, for example, a stainless-steel solid wire having the same outer diameter as that of the auxiliary wire 200 and the distal end portion of the core shaft 10.

As the auxiliary wire 200 has the configuration in which a plurality of strands made of stainless steel is twisted together, the breaking elongation of the auxiliary wire 200 is longer than the breaking elongation of a stainless-steel solid wire. Therefore, the slope of the second graph G2 is more gradual than the slope of the load and the amount of elongation (not illustrated) of a stainless-steel solid wire. More specifically, as illustrated in FIG. 2, the second graph G2 intersects with the first graph G1 in the plateau region (see LY in FIG. 2). This indicates the following.

a) When the amount of elongation of the guide wire 100 (the distal end portion of the core shaft 10, the auxiliary wire 200) is equal to or less than a predetermined value (LY in FIG. 2), the tensile stress is primarily applied to the distal end portion of the core shaft 10 as compared with the auxiliary wire 200. Therefore, the torque generated by a rotational operation, or the like, on the proximal end side of the core shaft 10 is transmitted to the distal end portion of the core shaft 10, and the operability of the distal end portion of the core shaft 10 is ensured. It is possible to prevent deformation, etc. of the distal end portion of the core shaft 10 in an unexpected direction due to the application of the tensile stress to the auxiliary wire 200.

b) When the amount of elongation of the guide wire 100 is more than the predetermined value (LY in FIG. 2), the tensile stress is primarily applied to the auxiliary wire 200 as compared with the distal end portion of the core shaft 10 before the distal end portion of the core shaft 10 reaches the yield point P1. This prevents breakage of the distal end portion of the core shaft 10. Therefore, even when the amount of elongation of the guide wire 100 exceeds the above predetermined value, the torque from the proximal end side of the core shaft 10 is transmitted to the distal end portion of the core shaft 10, and the operability of the distal end portion of the core shaft 10 is ensured.

As illustrated in FIG. 2, the breaking strength (F2) of the auxiliary wire 200 is higher than the breaking strength (F1) of the distal end portion of the core shaft 10 (the second requirement), and the breaking elongation (L2) of the auxiliary wire 200 is shorter than the breaking elongation (L1) of the distal end portion of the core shaft 10 (the third requirement). This may prevent the breakage of the distal end portion of the core shaft 10 unless a tensile load exceeding the breaking strength of the auxiliary wire 200 is applied. The breaking elongation (L2) of the auxiliary wire 200 is shorter than the elongation (LX) at the yield point P1 of the distal end portion of the core shaft 10 (the fourth requirement). This prevents the distal end portion of the core shaft 10 from reaching the yield point and maintains the elastic deformation state. This may prevent the occurrence of part replacement due to plastic deformation of the core shaft 10.

For example, in the configuration where the breaking strength of the auxiliary wire 200 is more than the breaking strength of the distal end portion of the core shaft 10, the auxiliary wire 200 is configured such that the breaking elongation (L2) of the auxiliary wire 200 is 70% or less, preferably 60% or less of the breaking elongation (L1) of the distal end portion of the core shaft 10. This may prevent the core shaft 10 from breaking before the auxiliary wire 200 and may prevent the loss of operability of the guide wire 100 when the distal end portion of the core shaft 10 breaks first.

A-3. Effect of Embodiment

As described above, in the guide wire 100 according to the present embodiment, the distal end portion of the core shaft 10 has a pseudoelastic property. Therefore, as compared with the configuration in which, for example, the distal end portion of the core shaft 10 is made of a material not having a pseudoelastic property, such as stainless steel, it is possible to prevent the breakage of the core shaft 10 when the distal end portion is elongated due to the tensile stress applied. The auxiliary wire 200 is arranged parallel to the distal end portion of the core shaft 10, and the auxiliary wire 200 is more flexible than the distal end portion of the core shaft 10 (the first requirement). Thus, according to the present embodiment, the auxiliary wire 200 may prevent the breakage of the core shaft 10, while it is possible to prevent a decrease in the flexibility of the distal end portion of the core shaft 10 due to the presence of the auxiliary wire 200.

According to the present embodiment, the breaking strength of the auxiliary wire 200 is higher than the breaking strength of the distal end portion of the core shaft (the second requirement). Thus, as compared with the configuration in which the breaking strength of the auxiliary wire 200 is equal to or less than the breaking strength of the distal end portion of the core shaft 10, the breakage of the core shaft 10 may be prevented more effectively.

According to the present embodiment, the breaking elongation of the auxiliary wire 200 is shorter than the breaking elongation of the distal end portion of the core shaft 10 (the third requirement). Thus, as compared with the configuration in which the breaking elongation of the auxiliary wire 200 is equal to or more than the breaking elongation of the distal end portion of the core shaft 10, the application of the tensile stress only to the core shaft 10 is prevented so that the breakage of the distal end portion of the core shaft 10 may be prevented more effectively.

According to the present embodiment, the breaking elongation of the auxiliary wire 200 is shorter than the elongation at the yield point P1 of the distal end portion of the core shaft 10 (the fourth requirement). This prevents the distal end portion of the core shaft 10 from reaching the yield point P1 and maintains the elastic deformation state of the distal end portion of the core shaft 10 and, as a result, plastic deformation of the distal end portion of the core shaft 10 may be prevented.

According to the present embodiment, the auxiliary wire 200 has the configuration in which a plurality of strands is twisted together (the fifth requirement). Thus, the flexibility of the auxiliary wire 200 is maintained, while the breaking strength of the auxiliary wire 200 may be improved.

B. Modification

The disclosure is not intended to be limited to the embodiment described above and may be modified to various forms without departing from the spirit thereof and may be modified as described below for example.

The configuration of the guide wire 100 according to the above embodiment is merely an example and may be modified in various ways. For example, although the core shaft 10 includes the small diameter portion 11, the tapered portion 12, and the large diameter portion 13 according to the above-described embodiment, the core shaft 10 may omit at least one of the three portions or may include another portion in addition to the three portions. Specifically, the core shaft 10 may be configured to have substantially the same outer diameter over its entire length without tapered portion 12 or may be configured such that the tapered portion 12 has a shape so as to extend to the distal end of the core shaft 10 without the small diameter portion 11.

According to the above-described embodiment, the coil body 20 has the configuration of the tightly wound strand, but the coil body 20 may also have the configuration of a coarsely wound strand. The coil body 20 has a configuration formed in a hollow cylindrical shape by spirally winding one strand, but may also have a configuration formed in a hollow cylindrical shape by spirally winding a plurality of strands, may have a configuration formed in a hollow cylindrical shape by spirally winding one twisted wire formed by twisting a plurality of strands, or may have a configuration formed in a hollow cylindrical shape by spirally winding a plurality of twisted wires formed by twisting a plurality of strands. The guide wire 100 may also be configured without the coil body 20.

According to the above-described embodiment, the configuration may be such that the proximal end of the auxiliary wire 200 is joined to the large diameter portion 13 of the core shaft 10. The auxiliary wire 200 may have a configuration formed by one solid wire formed to be thin with a material having a high tensile force than the core wire, or may have a configuration formed by twisting three or more strands. The auxiliary wire 200 may also have a configuration that does not satisfy at least one of the second requirement to the fifth requirement described above.

The material of each member according to the above-described embodiment is merely an example and may be modified in various ways. For example, the configuration may be such that the auxiliary wire 200 and the distal end portion of the core shaft 10 are made of the same material and the outer diameter of the auxiliary wire 200 is smaller than the outer diameter of the distal end portion of the guide wire 100 so that the auxiliary wire 200 is more flexible than the distal end portion of the core shaft 10.

In the configuration described according to the above embodiment, the auxiliary wire 200 is a twisted wire obtained by twisting a plurality of strands together, but the configuration may be such that, instead of the twisted wire, a plurality of straight strands is bundled to form one wire.

The invention claimed is:

1. A guide wire comprising:
a core shaft including a distal end portion having a pseudoelastic property;
a tip joined to a distal end of the distal end portion of the core shaft; and an auxiliary wire arranged parallel to the distal end portion of the core shaft, the auxiliary wire having a distal end joined to the tip and a rear end joined to the core shaft,
wherein the auxiliary wire is more flexible than the distal end portion of the core shaft,
a breaking strength of the auxiliary wire is higher than a breaking strength of the distal end portion of the core shaft,
a breaking elongation of the auxiliary wire is shorter than a breaking elongation of the distal end portion of the core shaft, and
the breaking elongation of the auxiliary wire is shorter than an elongation at a yield point of the distal end portion of the core shaft.

2. The guide wire according to claim 1, wherein the auxiliary wire comprises a plurality of strands twisted together.

3. The guide wire according to claim 1, wherein the pseudoelastic property is an elastic property that occurs in a mechanism other than elasticity resulting from changes in interatomic spacing.

4. The guide wire according to claim 1, wherein the pseudoelastic property is at least one of transformation pseudoelasticity and twinning pseudoelasticity.

* * * * *